United States Patent [19]

Andersen

[11] 4,226,231
[45] Oct. 7, 1980

[54] FRACTURE BOARD

[76] Inventor: Arthur L. Andersen, Rte. 1, Box 1891, Anderson, Calif. 96007

[21] Appl. No.: 958,736

[22] Filed: Nov. 8, 1978

[51] Int. Cl.³ .............................................. A61F 13/00
[52] U.S. Cl. ................................................... 128/134
[58] Field of Search ................................ 128/132–135, 128/DIG. 15, 171, 87 B; 5/82 R

[56] References Cited

U.S. PATENT DOCUMENTS

| | | | |
|---|---|---|---|
| 3,034,502 | 5/1962 | Lund | 128/134 |
| 3,358,141 | 12/1967 | Hoffmann et al. | 128/134 |
| 3,526,222 | 9/1970 | Dreibelbis | 128/134 |
| 3,889,668 | 6/1975 | Ochs et al. | 128/134 |
| 4,127,120 | 11/1978 | Applegate | 128/DIG. 15 |
| 4,141,368 | 2/1979 | Meyer | 128/87 B |

Primary Examiner—Lawrence W. Trapp
Attorney, Agent, or Firm—Mark C. Jacobs

[57] ABSTRACT

A fracture board for use by emergency personnel for immobilizing an injured patient. The board features a head portion and a lower portion. The lower portion has a plurality of longitudinally extending spaced slots, a pair of angular slits extending toward the centerline from the top edge, and a pair of bottom notches. The board can be made of fiberglass and one embodiment includes a rigid foam insert.

17 Claims, 9 Drawing Figures

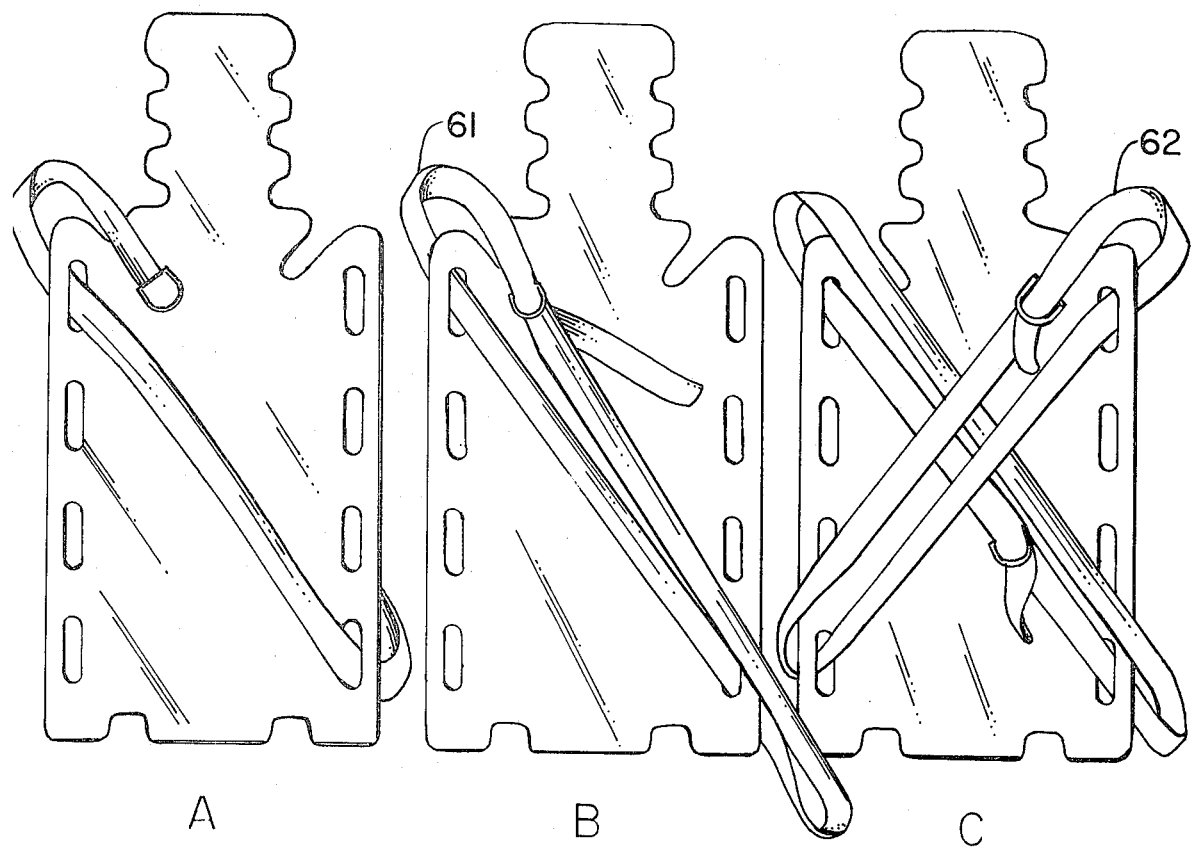
FIG. 7
A  B  C
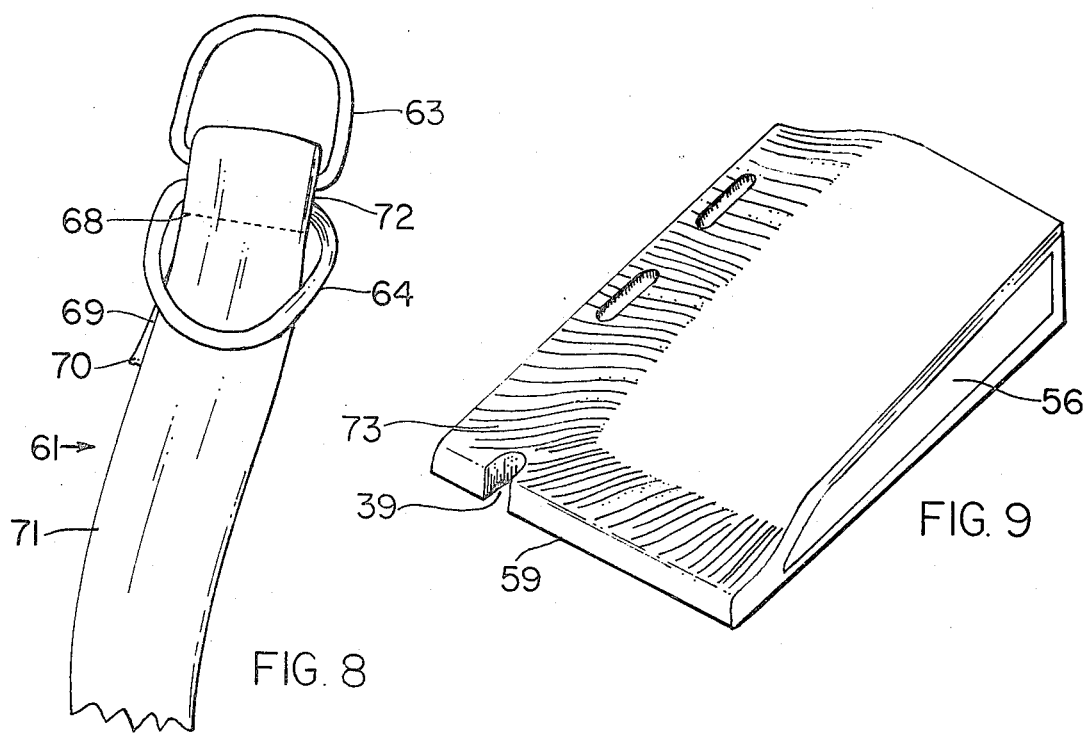
FIG. 8
FIG. 9

FRACTURE BOARD

BACKGROUND OF THE INVENTION

1. Field of Invention

The handling of injured persons especially those who have been hurt in industrial or in vehicular traffic accidents, requires special care in removing and carrying such persons to a location equipped to administer medical treatment, such as hospitals or emergency centers.

A need exists for a rescue apparatus which may be used in extricating accident victims safely from an accident site and transporting them to hospitals. Spin boards have been used to hold fracture patients immobilized heretofore. Use of such boards is reviewed in the Bulletin of the American College of Surgeons, vol. 52 No. 3.

The board structure of this invention has been designed to comply with American College of Surgeons recommendations, particularly in regard to minimum overall length for handling possible spinal injuries; while being dimensioned for convenience, speed and safety.

2. Description of the Prior Art

A preliminary search reveals the U.S. Pat. Nos. to Warden, 2,141,100 of Dec. 20, 1938; Phillips, 3,469,268 of Sept. 30, 1969 and Hughes, 2,511,061 of June 13, 1960. Other U.S. Pat. Nos. known to applicant include Hughes 2,811,061; Ochs 3,889,668 Klippel 3,566,422 and Matthew 3,707,734. None of these references, either singlely or in combination, show or suggest the invention of this application.

SUMMARY OF THE INVENTION

The improved fracture board structure of this invention provides a device for use by hospital and/or ambulance attendants at an emergency or accident site in the splinting and immobilizing of an injured patient against possible further cervical or spinal trauma during his removal and transportation to a treatment facility.

One object of the present invention is to provide a new and improved fracture board usable in situations described above.

Another object of the present invention is to provide a new and improved light weight fracture board.

Another object of the present invention is to provide a new and improved fracture board which is comparatively easy of application to a victim.

Still another object of the present invention is to provide a new and improved fracture board which is capable of being employed while an attendant is working in an extremely confined space.

Other objects of the invention will in part be obvious and will in part appear hereinafter.

The invention accordingly comprises the product possessing the features, properties and relation of components which are exemplified in the following detailed disclosure, and the scope of the application of which will be indicated in the claims.

For a fuller understanding of the nature and objects of the invention, reference would be had to the following detailed description taken in conjunction with the accompanying drawings. In the discussion herein like numbers will be used to refer to like parts in the several embodiments of this invention.

BRIEF DESCRIPTION OF THE DRAWINGS

FIG. 7 illustrates a typical two-strap patient securing procedure such as would be employed with abdominal injuries.

FIG. 8 illustrates a belt employable in the strapping technique depicted in FIG. 7.

FIG. 9 is a fragmented sectional view of the embodiment of FIG. 4.

DESCRIPTION OF THE PREFERRED EMBODIMENT

Figure 1:
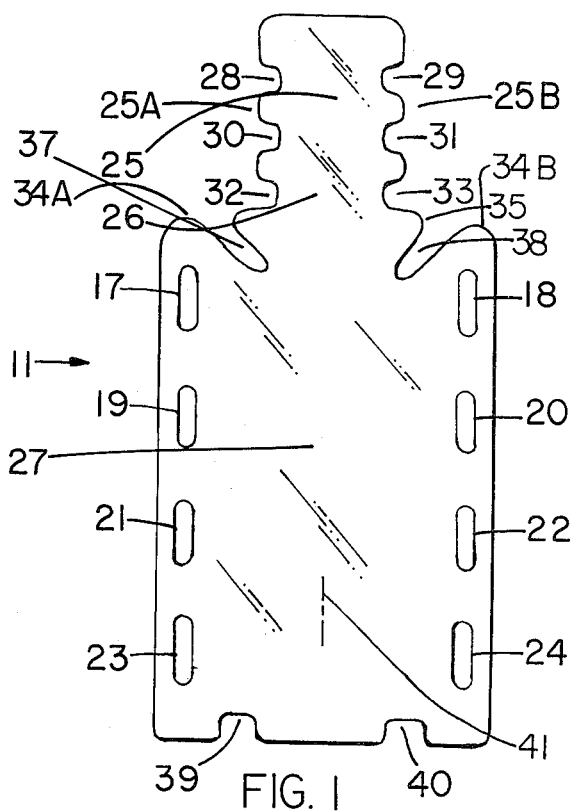
FIG. 1 is a top plan view of fracture board of this invention.

In detail as is shown in FIG. 1, the board 11, of this invention comprises a unitary structure comprising a plurality of superposed laminated equidimensional in length and width glass fibre sheets generally resembling two abutting rectangles which abut from the centreline of the small side of each, thereby roughly approximating the contours of the head, shoulders and torso of the human body. The top portion is of a multi-T shaped configuration.

The top portion 25 includes a plurality of spaced apart notches 28,30, and 32 along one side thereof, and a plurality of correspondingly spaced apart notches 29,31, and 33 on the other side elevation thereof. It is preferred that the inboard distance between all of the left hand side and all of the right hand side 25B notch pairs, 28,29; 30,31 and 32,33 be the same. Stated another way, the depth of each notch as designated by D should be the same. The elevation between each notch as designated by E may be the same or different. This elevation should however be the same on both sides 25A and 25B of head or top portion 25.

The torso portion 27, also generally rectangular includes a pair of inwardly disposed slits, of equal dimension, emanating from the top corners 34A and 34B of said torso portion 27. These slits designated 37,38 are angularly disposed at about a 45° angle and extend inward toward the vertical centreline of the board 11. Slits 37 and 38 are rounded at their interior ends and terminate at a point slightly further from the vertical centreline of the board 11 than the extension of width of said top portion 25 at point 35 from said centreline, 41. Slits 37,38 may be employed as belt receiving slits, depending upon the configuration of belt tieing being employed. Details on belt tieing will be recited supra. Any strap means may be used to secure the patient to the panel 11.

Lower portion 27 includes a plurality of spaced pairs of oblong slots, rounded on the ends, 17,18; 19,20; 21,22; and 23,24. These oblong longitudinally spaced slots ae preferably all laterally equidistant from the vertical centreline 41. There may be employed a greater or lesser number of such spaced pairs as may be desired. The oblong slots aforesaid are employed as belt receiving means for securing the injured patient to the fracture board of this invention, 11. Though 8 slots are preferred, more or less can be used.

Along the bottom edge of said board 11, there are a pair of spaced apart rounded corner bottom notches 39 and 40. These notches 39 and 40 are equidistant from the vertical centreline 41. Bottom notches 39,40 may also be employed as belt receiving means.

Figure 3:
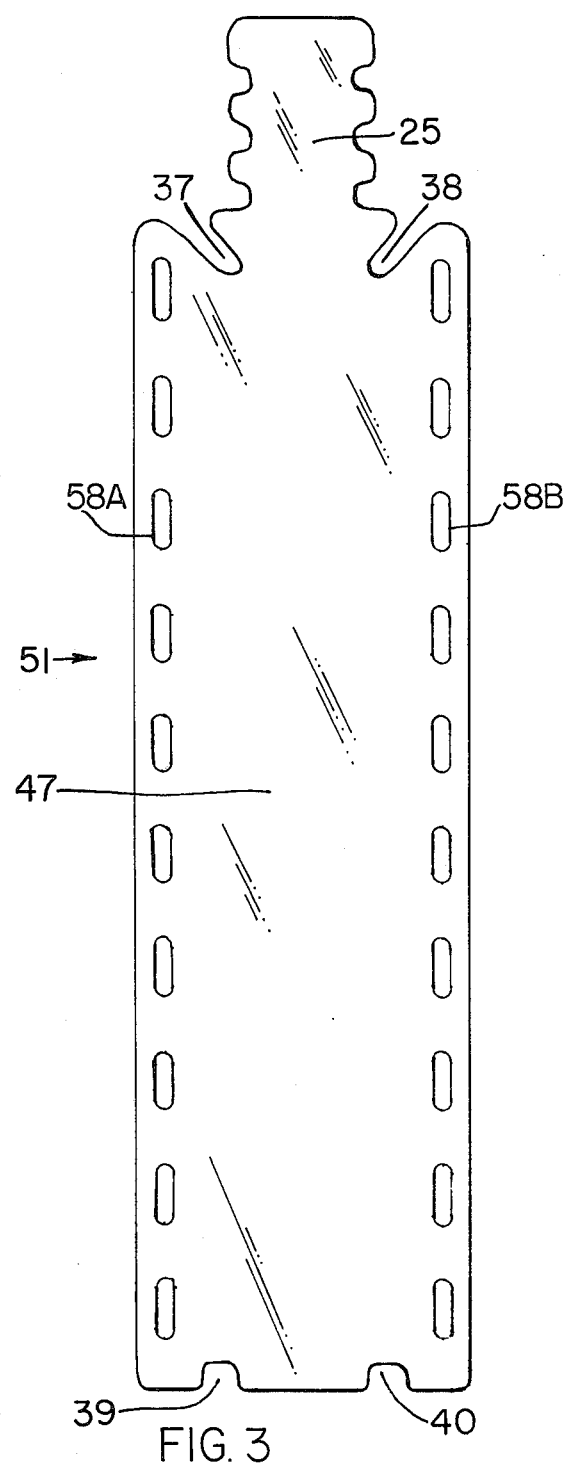
FIG. 3 is a top plan view of another embodiment of this invention.

In FIG. 3 there is shown a full-length body board 51 of the same general configuration as the board 11 of FIG. 1. The board 51 includes a top portion for the head 25, as previously described, and a lower portion 47 of the same general configuration as torso portion 27, only longer and with more spaced apart, rounded corner, oblong longitudinally, pairs of slots 48A and 48B than are found in the board 11. Board 51 also includes bottom notches 39 and 40 as previously described. Preferably there are 18 slots 48.

Figure 2:
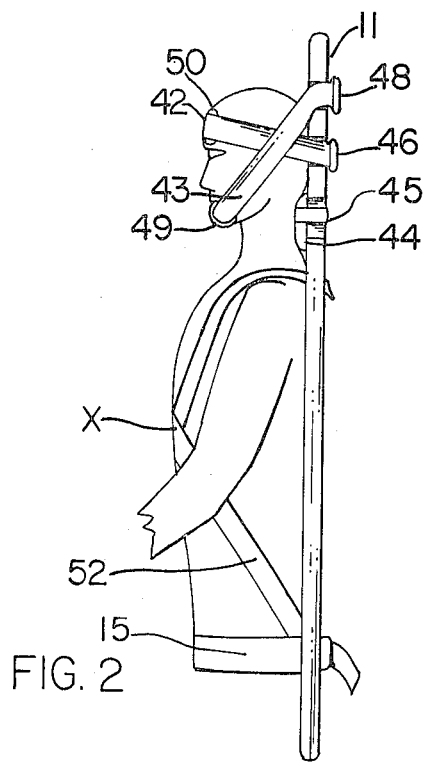
FIG. 2 is a side view of an embodiment of the fracture board of this invention, with the "victim" shown in phantom. The opposite side view is a mirror-image.

FIG. 2 illustrates the ease with which the belting may be employed for the critical immobilization of the neck back and head of the patient. It is seen that these are the most critical areas of the body such that movement of previously injured areas can be extremely detrimental to the well being of the patient.

Since the total strapping of the head is readily understood by reference to FIG. 2, no other explanation of the head belts will be set out other than is discussed herein. The body belting technique is the basic single strap technique, the front view of which is seen in FIG. 5 and the rear view of which is seen in FIG. 6.

In the FIG. 2, head strap 42 and chin strap 43 are shown crossed in a suitable position to stabilize the neck, head and upper back of the patient. While shown crossed, the practitioner may depending upon the type of injury prefer to employ a straight belting technique, and such is entirely feasible with the device of this invention. Straps 42 and 43 are secured at the rear side of board top portion 25 by buckle means 46 and 48 respectively. Acting in cooperation with head strap 42 and chin strap 43 is neck pad 44 secureable in the desired position by neck pad strap 45. The head strap 42 and chin strap 43 are held in a relative location with respect to the patient by being disposed in any two pairs of the notches, preferably 28-29 for 43, and 32,33 for strap 42 respectively. For patient comfort there may be employed a chin pad 49, secured slidingly to strap 43 for adjustment to the necessary location on any individual person. The head strap 42 is preferably provided with a soft padding 50. The chin pad 49 aforesaid also helps to prevent side to side movement of the head. Neck pad 44 is made of soft resilient material such as urethane foam that is self skinned, or covered with soft cloth.

Figure 5:
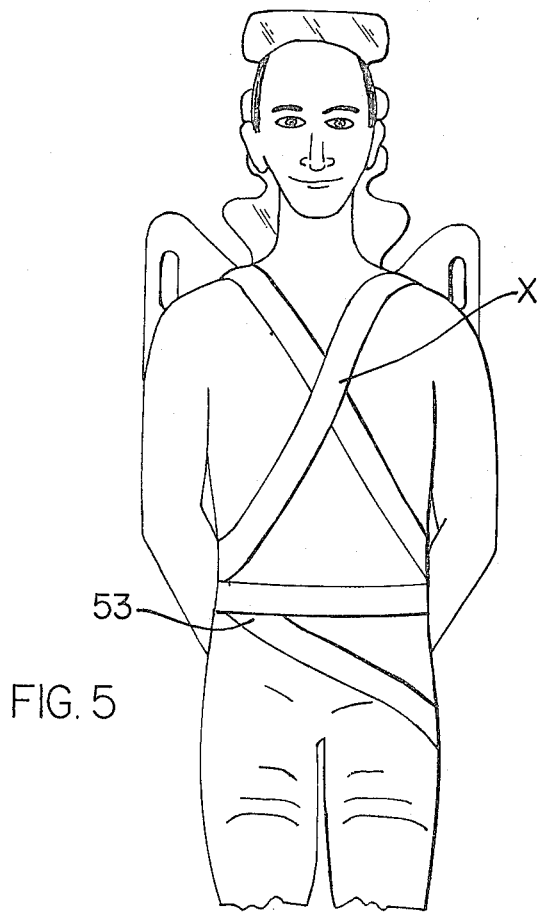
FIG. 5 is a fragmentary perspective view sharing a typical manner of using the embodiment of FIG. 1 in the splinting of a patient in a sitting posture wherein only a single strap is used.
Figure 6:
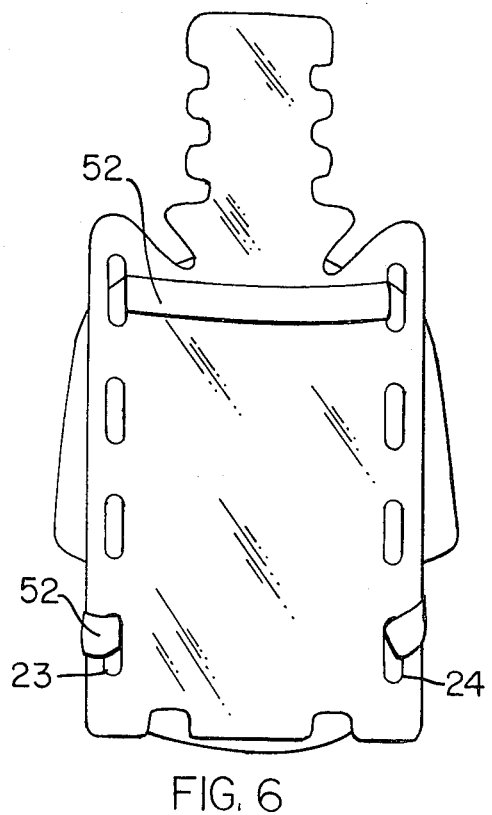
FIG. 6 is a back view of the splinting of a patient using the board and strapping technique of FIG. 5.

For securing the body of the patient there is provided a long body strap 52 which is seen to be crossed over itself at point X in the shape of an x in the front of the body, over each shoulder, through oblong slotted openings 17,18; down and around the waist area at the sides of the body, through slots 23 and 24, and then back around the entire waist area via the edges of the board adjacent slots 23 and 24, (See FIG. 6), terminating in buckle 53, as seen in FIG. 5. FIG. 5 illustrates the crossover pattern aforesaid, but the patient is shown without the head being secured. A suitable length for the body strap 52 is about 114 inches to 144 inches. The body strap and the other straps aforementioned may be from 1.5 to 2.0 inches wide, or wider if desired.

Figure 4:
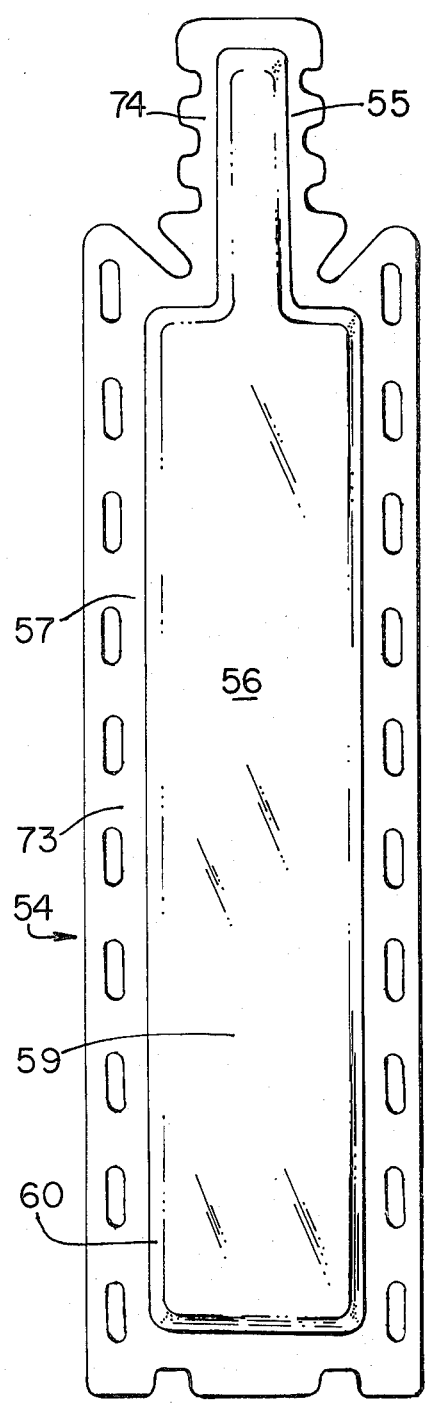
FIG. 4 is a top plan view of yet another embodiment of this invention constituting a modified version of the device of FIG. 3.

In FIG. 4, there is shown an alternate version of the embodiment of FIG. 3. The total body board 54 comprises a head section 55 and a body and leg section 57. The notches and oblong rounded corner spaced apart slots are the same as in the embodiment of FIG. 3. However, there is disposed in the board 54 along the centreline and extending outwardly toward the edges of the top and bottom sections thereof, a foam insert 56 preferably comprising a two pound density closed cell rigid urethane, which is intended to strengthen the board and keep it from bowing. See also FIG. 9.

Whereas the boards of FIGS. 1 and 3 comprise only superposed layups of fiberglass material, the board 54 of this embodiment is constructed with a preformed precut foam insert in the manner to be described infra.

Since the art of fiberglass molding is old and well known attention will be paid only to the details of the process for making the instant boards.

ALL-FIBERGLASS BOARDS

Using two half molds, A and B, sized slightly larger than the instant board, each is sprayed with white gel coat. Due to possible wounds on the patient, no lead or other poisonous pigment is employed in this outermost coat. Then two 3 oz. mats are layed in, one after the other, in the first side of the mold. A gel-coated second half of mold B is layed up with three layers of 3 oz. mat. This gives us five layers of 3 oz. mat.

The molds are then placed together with guide pins and put under a press, and pressed at 350 PSI. Guide pins only go through the outside edge or the mold, not through the board.

After the board is compressed, the molds are clamped, removed from the press and placed in a drying room which is heated to 100° F. Later they are removed from the molds and the tips from the squeeze holes are cut off and touched up if needed. When the board is removed, the gel coat sticks to the board. Working time is approximately 20 to 30 minutes. Drying time is approximately one hours.

The long board without the foam insert is made in a similar manner.

The foam filled board as shown in FIGS. 4 and 9 is prepared in a similar manner. A gel coat is applied to the mold which is a one-piece bottom section only and is allowed to set up. A layer of resin-coated 3 oz. mat is applied over the gel coat. A second layer of 3 oz. mat is applied over the previous layer. A two pound density closed cell polyester urethane foam insert that is preshaped is dipped or otherwise coated with the resin on both sides and applied with the large bevel down. Three more layers of resin-soaked fiberglass mat are applied over the foam. The slits (holes) and a rough shape of the board are cut out with a sharp cutting tool before curing has been completed.

A gel coat layer is applied over the top side of the board while it is still in the mold.

After all layers are dry but tacky, the board is trimmed with a razor knife to the desired shape.

It is to be specifically noted that unlike the all-fiberglass board without the foam, the mold here is only a one-piece unit. Here also, the elongated holes are cut into the board after the laying up operation. In the all-fiberglass boards each mat is precut to shape in the areas of the elongated holes, and the mold is shaped accordingly. Also, no clamping or pressure is used with the foam insert units.

Suitable boards of foam-filled and all-fiberglass have been prepared using a gel coat which is chemically the same as the resin, namely an unsaturated orthophthalic acid polyester with added styrene monomer. Other polyester resins will perform equally satisfactorily if such a resin is designated a Type B resin. A Type A resin as this term is known in the art is not suitable for the multi-layer layups of this invention. Among the catalysts found suitable for the resin curing are the organic peroxides and especially methyl ethyl ketone peroxide in dimethyl phthalate.

The pigment used in the gel coat is $TiO_2$ usually in an amount of 5% to 6% of an FDA grade.

In practice it has been found that foam-filled boards of a total thickness of about $\frac{3}{4}''$ and including an upraised portion, tpaering to about $\frac{1}{4}''$ thickness in the all-fiberglass areas only give satisfactory field operational results.

The all-fiberglass boards of this invention are generally about $\frac{1}{4}''$ thick, and are thus relatively light in weight. More details on the configuration and dimensions of the foam-filled board of FIG. 4 are recited later in this application.

In FIGS. 5 and 6 there is shown the basic single strap securing technique employed with a sitting patient using the short board. The patient is secured in any of many ways. A typical deplyment of the belting 52 is seen in the shoulder-to-waist crossover as seen in FIGS. 5 (front) and 6 (rear). The belt could also be reversibly threaded such that the horizontal portion as seen in FIG. 6 would be on the inward side of the board as by going around the outside edge of the board from the shoulders and then through slots 17 and 18, if such is desired. The technique of FIGS. 5 and 6 is generally referred to a basic single strap securing technique.

Another technique not shown but easily understandable is the single strap backpack technique which would deploy the belt over each shoulder, from the rear of the board via slits 37 and 38, under the arm pits, then through slots 19 and 20 from the front of the board, generally vertically downward on the rearside thereof and exiting through slots 21 and 22 to the front of the board for joining of the ends of the belt.

These are but two of many techniques that may be employed by skilled artisans to secure persons to the boards of this invention.

In FIGS. 7a, 7b and 7c there is depicted the use of a two belt restraining system, based upon the use of two nylon seat belt of an automobile type belts 61 and 62. Belt 61 is received in slots 17 and 24 and slit 37; while belt 62 is received in slots 18 and 23 and slit 38. Each belt being the same for use in the FIG. 7 procedure, only one of which is shown; namely 61 in FIG. 8.

Belt 61 includes an elongated section 71 that is the main section, and a short folded over section 69, which is secured to the main section 71 at least at the rows of stitches 68 and 70. Held within the folded over section 72, but free to orient therein forwardly and backwardly, as shown in the diagram are a pair of D-rings 63 and 64.

While a patient is not shown in FIG. 7, for ease in understanding the strapping procedure, one should assume the presence of such a patient. Thus to employ this two strap procedure as with possible abdominal injuries, the practitioner should start at the left shoulder and lay the D-rings 63 and 64 on the patient's chest. The belt 61 id fed over the right shoulder and through the slot 17 from the rear of board 11, across the chest to slot 24, pass rearwardly therethrough, around the side 11B adjacent to 24, up to and through the one D-ring 63; then using a second strap pass over the left should, lay D-ring on the patient's chest, through 18 from the rear, across the chest, down to and through 23 from the front, up over the board and back across the chest to the D-ring. The excess strap is used to secure the hand by tieing a knot. This is done to keep the hand out of the way while moving the patient.

Belt 62 is fed in like manner through the slots and slit aforementioned in the same pattern.

For best results, belts 61,62 should be about 2 inches wide and 11 to 11.5 feet long.

FIG. 8 illustrates the preferred form of belt used in the strapping techniques illustrated in FIGS. 2, 5 and 6. Belt 61 comprises an elongated main section 61 which in preparation is folded over two D-shaped buckles 63 and 64, which are disposed within gap 72 and which buckles, while held constricted within gap 72 by stitch row 68 which secures folded portion 69 to main section 71, said buckles are pivotally orientable within their confines, as well as being capable of sliding toward each other in a horizontal plane since the gap area is sized for said buckles 63,64 to be slightly spaced apart from each other as is seen in the Figure. Stitch row 70 normal to the length of the belt secures the end of the folded over portion 69 at its terminus to main section 71.

The buckles employed are state of the art D-shaped buckles, preferably. Obviously other tightening means such as snaps on the belt will function in like manner to hold the patient to the panel.

In the description aforesaid the straps and belts that are described and shown in the figures are of the typical car seat-belt-type fastening means which may be secured with a buckle as is known in the art. In addition, the belting mechanism employed in aircraft seatbelt restraining systems can also be employed. Such systems utilize a belt with a pivotally orientable securing means to frictionally engage the belt and secure it in position at a desired location on the length of the belt. Car seatbelts on the other hand, as is known, employ a male and female interlocking member on the terminal ends of the belt. In addition to either of these, one may employ a tape-type fastening means as typified by an interlocking fabric system such as by providing the belt at least for the length of overlap with a layer of VELCRO ® on one side and the corresponding VELCRO ® layer at the terminal portion of the belt on the undersign thereof. VELCRO ® is a product of VELCRO-S.A. FRIEBOURG, Switzerland and constitutes a velvet-type fabric comprising a structure including a plurality of auxiliary warp threads of a synthetic resin material in the form of raised pile threads. The terminal portions of which are at least in part in the form of material-engaging hooks. Reference is made to U.S. Pat. No. 2,717,437.

It is important in using the fracture boards of this invention that only trained personnel use them otherwise the injured person is liable to suffer further harm. Thus such trained persons would readily recognize the fact that straps should never be placed over a joint such as the knee or ankle. Such personnel also know that if it is necessary to secure the head, that is secured last and released first.

In using the boards of this invention one should commence the securing procedure at the shoulders and work down the body, and then finally secure the head if necessary.

USE OF THE BOARDS

The FIG. 1 short back board is preferably about 36" long, 16" wide at the widest point, and 5" at the neck (the narrowest point). It is used for the removal of patients who are suspected of having back and/or neck injuries.

The board is placed behind the patient and he is secured by the belts to the board as discussed elsewhere herein.

The board has been strength tested in actual-use testing and also by driving a 36,000 lbs. fire truck up over it. This has been done with both tires on the rear axle of the truck or roughly 6,000 lbs. per wheel (12,000 total). The board did crack, but was still strong enough to support the weight of a person of 220 lbs. with out any difficulties.

It is seen that the resin impregnated fiberglass fracture boards of this invention will provide years of service.

The long board in FIG. 3 is preferably about 72" long and the same shape as the short board of FIG. 1. It will not therefore be discussed in detail. The long board is used for transportation from accident to ambulance, and from gurney to X-ray table, etc. The patients can be strapped on the long board for moving long distances or over rought country terrain. The board has ten tie-down elongated holes 58A and 58B on each side along the length of the board. Shoulder 37,38 and feet cutouts 39,40 are used for securing the patient to the board.

Preferably when the board is being employed four people should carry the patient since when only two carry the board there is a slight bowing effect created. However, doctors are quick to point out that this is not enough deviation from flat to cause injury to the patient.

The foam-filled long board of FIG. 4 is of the same general configuration as the long all-fiberglass board and is used for similar purposes in a similar manner.

The covered foam member 56 at the face of patient contact is preferably between 8" and 9" wide. The central section is an upraised portion 59 that tapers downwardly and outwardly 60, at about a 45° angle to the all-fiberglass periphery portion 73 of body and leg section 57. The preferred total width of the foam covered upraised section at its junction with the all-fiberglass portion 73 of section 57 is between 10" and 11 inches. See FIG. 9 which shows the tapering of the upraised portion.

In head section 55 the covered insert portion 59 is from 2" to 3" wide at the head contact area, tapering to a width of about 4" to 5" wide in the all-fiberglass section of the head section 55, designated 74.

In summary the instant boards possess many new features and improvements over the prior art fracture board.

The multi-T configuration of the top portion of all embodiments of the invention is an improvement over any previous board. The notches 28,29 are preferably approximately 1½" wide by 1¼" deep and are made this way to insure against any slip of bandage or straping used to secure the head and neck to the board. In prior art board there was no way to insure against this. The neck 26, of the board, ie. inside the notches, is made narrower than in any prior art board to insure against improper head movement. The neck of the board is preferably about 5" wide. This makes it easier to secure a patient to the board without using unnecessary equipment and padding to hold the head in place. After applying the cervical collar to the patient, the head is placed against the board without movement, and the upper torso is secured to the board. Then the head is secured to the board using roller bandaging on straps as shown in FIG. 2 for example.

The reduced thickness over prior art boards renders it more easily placeable behind a patient in a suppine position or in a cramped situation as a motor car accident.

The inwardly disposed slits in the lower portion of both the long and short boards and in the retention of the straps and/or bandages prevent slippage thereof.

The bottom notches also are to prevent slippage of the belt(s) used to secure the patient to the board, and/or any bandages used for the same or other purposes. These notches help secure the strapping especially during times when the patient is being moved from the accident scene.

Since the board is substantially impenetrable by foreign matter such as nails, stones, dirt, etc. even after usage, foreign objects will not show up in X-ray images of the patient secured to the boards of this invention.

Since certain changes may be made in the above apparatus, without departing from the scope of the invention herein involved, it is intended that all matter contained in the above description and shown in the accompanying drawings shall be interpreted as illustrative and not in a limiting sense.

I claim:

1. A fracture board for use in the handling of an injured person at the site of an accident, and for use in the lifting, carrying and transportation of said injured person to a treatment facility, said board comprising a panel having a head portion integrally connected to a lower portion, said portions taken together forming an outline conforming to the outline of the human body,
   said lower portion having a plurality of laterally, evenly spaced pairs of slots extending longitudinally and spaced apart from each other, and
   a pair of slits emanating from the top edge of the lower portion angularly disposed toward the vertical centerline of said portion, and
   a pair of spaced apart notches along the bottom edge of said board,
   and strap means for securing the injured person to the panel adapted to pass over and around the body and through the slots, slits and notches, and having tightening means to hold the injured party to the panel.

2. The fracture board of claim 1 wherein the head portion is of a multi-tee shaped configuration.

3. The fracture board of claim 1 wherein the board comprises a plurality of adhered layers of cured resin impregnated fiberglass.

4. The fracture board of claim 2 wherein the board comprises a plurality of adhered layers of cured resin impregnated fiberglass.

5. The fracture board of claim 2 wherein the strapping means is one or more belts each with a D-shaped buckle thereon.

6. The fracture board of claim 1 wherein the lower portion is sized to hold both the torso and legs of the injured patient.

7. The fracture board of claim 2 wherein the lower portion is sized to hold both the torso and legs of the injured patient.

8. The fracture board of claim 7 wherein the board comprises a plurality of adhered layers of cured resin impregnated fiberglass.

9. The fracture board of claim 7 wherein there are nine pairs of spaced apart oblong slots.

10. The fracture board of claim 1 wherein the central section thereof is upraised from the balance of the panel and tapers downwardly and outwardly to the periphery of the panel.

11. The fracture board of claim 10 wherein the upraised central section is of resin impregnated fiberglass adhered to a rigid foam section insert.

12. The fracture board of claim 11 wherein the board is sized to hold both the torso and legs of the patient.

13. The fracture board of claim 11 wherein the foam insert is a closed cell polyurethane foam.

14. The fracture board of claim 13 wherein the strapping means is one or more belts each with a D-shaped buckle thereon.

15. The fracture board of claim 13 wherein the strapping means is one or more belts each of which has as a tightening means, means, releasably engageable from itself by a snap-type pressured-adhered hook and loop system.

16. A fracture board for use with injured persons comprising a panel having a multi-tee-shaped configured head portion integrally connected to a torso portion, said portions taken together forming an outline conforming to the outline of the human body, said lower portion having four pairs of laterally, evenly spaced pairs of slots extending longitudinally and spaced apart from each other, and a pair of slits emanating from the top edge of the lower portion angularly disposed toward the vertical centerline of said portion, and a pair of spaced apart notches along the bottom edge of said board, and strap means for securing the injured person to the panel adapted to pass over and around the body and through the slots, slits and notches, and having tightening menas to hold the injured party to the panel.

17. The fracture board of claim 16 wherein the board comprises a plurality of adhered layers of cured resin impregnated fiberglass.

* * * * *